United States Patent [19]

Walther et al.

[11] Patent Number: 4,503,060
[45] Date of Patent: * Mar. 5, 1985

[54] 3-IMINO-3H-DIBENZO-[c,f]-IMIDAZO-[1,5-a]AZEPINE PHARMACEUTICALS

[75] Inventors: Gerhard Walther, Bingen; Claus Schneider, Ingelheim am Rhein; Karl-Heinz Weber; Armin Fügner, both of Gau-Algesheim, all of Fed. Rep. of Germany

[73] Assignee: Boehringer Ingelheim KG, Ingelheim, Fed. Rep. of Germany

[*] Notice: The portion of the term of this patent subsequent to Feb. 2, 1999 has been disclaimed.

[21] Appl. No.: 410,006

[22] Filed: Aug. 20, 1982

[30] Foreign Application Priority Data

Sep. 2, 1981 [DE] Fed. Rep. of Germany ....... 3134672

[51] Int. Cl.³ .................... A61K 31/55; C07D 487/04; C07D 491/04; C07D 495/04
[52] U.S. Cl. ............................... 514/214; 260/239 D; 260/245.6; 260/330; 260/330.7; 514/215
[58] Field of Search .................. 260/245.6; 424/273 R

[56] References Cited

U.S. PATENT DOCUMENTS 3,860,606 1/1975 Van Der Burg ................. 260/245.6
4,313,931 2/1982 Walther et al. ................. 260/245.6

Primary Examiner—Alton D. Rollins
Attorney, Agent, or Firm—Hammond & Littell, Weissenberger & Dippert

[57] ABSTRACT

Compounds of the formula

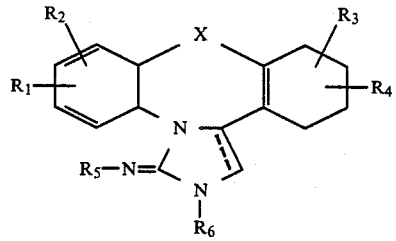

wherein
$R_1$, $R_2$, $R_3$ and $R_4$ are each hydrogen, halogen, alkyl of 1 to 6 carbon atoms or alkoxy of 1 to 6 carbon atoms;
$R_5$ is hydrogen, alkyl of 1 to 6 carbon atoms or alkenyl of 3 to 6 carbon atoms;
$R_6$ is alkyl of 1 to 6 carbon atoms, alkenyl of 3 to 6 carbon atoms, phenyl, halo-phenyl, lower alkyl-phenyl, or lower alkoxy-phenyl or

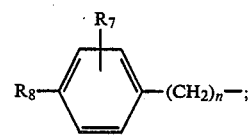

$R_7$ and $R_8$ are each hydrogen, halogen, alkyl of 1 to 6 carbon atoms or alkoxy or 1 to 6 carbon atoms;
n is an integer from 0 to 4, inclusive;
x is —O—, —S—, or —CH$_2$—; and the broken line between the 10 and 13b-positions indicates a single or double bond;

and non-toxic, pharmacologically acceptable acid addition salts thereof; the compounds as well as their salts are useful as antiallergics and antithrombotics.

5 Claims, No Drawings

3-IMINO-3H-DIBENZO-[c,f]-IMIDAZO-[1,5-a]-AZEPINE PHARMACEUTICALS

This invention relates to novel heterocyclic compounds and acid addition salts thereof, to methods of preparing these compounds, to pharmaceutical compositions containing them as active ingredients, and to methods of using them as antiallergics and antithrombotics.

More particularly, the present invention relates to a novel class of tetracyclic heterocyclic compounds represented by the formula

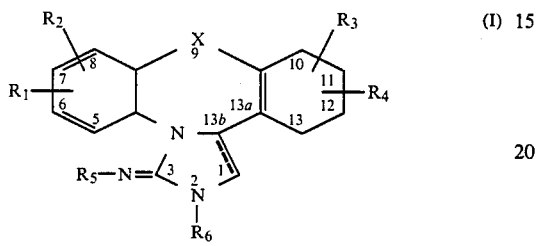

wherein
- $R_1$, $R_2$, $R_3$ and $R_4$ are each hydrogen, halogen, alkyl of 1 to 6 carbon atoms or alkoxy of 1 to 6 carbon atoms;
- $R_5$ is hydrogen, alkyl of 1 to 6 carbon atoms or alkenyl of 3 to 6 carbon atoms;
- $R_6$ is alkyl of 1 to 6 carbon atoms, alkenyl of 3 to 6 carbon atoms, phenyl, halo-phenyl, lower alkyl-phenyl, or lower alkoxy-phenyl or

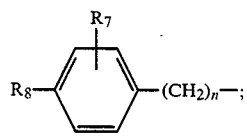

$R_7$ and $R_8$ are each hydrogen, halogen, alkyl of 1 to 6 carbon atoms or alkoxy of 1 to 6 carbon atoms;
n is an integer from 0 to 4, inclusive;
X is —O—, —S— or —CH$_2$—; and the broken line between the 1- and 13b-positions indicates a single or double bond;
and non-toxic, pharmacologically acceptable acid addition salts thereof.

The compounds of the formula I comprising an asymmetric carbon atom and their acid addition salts may exist as racemates, as pure enantiomers or as mixtures containing varying proportions of the enantiomers.

Substituents $R_1$ through $R_8$ in formula I may be identical to or different from each other, and the carbon chain of the alkyl, alkoxy and alkenyl variants thereof may be straight or branched.

Specific examples of the alkyl variants and the alkyl moiety of the alkoxy variants are the following: —CH$_3$, —C$_2$H$_5$, —CH$_2$—CH$_2$—CH$_3$, —CH(CH$_3$)$_2$, —(CH$_2$)$_3$—CH$_3$, —CH$_2$—CH(CH$_3$)$_2$, —CH(CH$_3$)—C$_2$H$_5$, —C(CH$_3$)$_3$, —(CH$_2$)$_4$—CH$_3$, —CH$_2$—CH$_2$—CH(CH$_3$), —CH$_2$—CH(CH$_3$)—C$_2$H$_5$, —CH(CH$_3$)—CH$_2$—CH$_3$, —CH$_2$—C(CH$_3$)$_3$, —C(CH$_3$)$_2$—C$_2$H$_5$, —CH(CH$_3$)—CH(CH$_3$)$_2$, —(CH$_2$)$_5$—CH$_3$, —(CH$_2$)$_3$—CH(CH$_3$)$_2$, —CH$_2$—CH$_2$—CH(CH$_3$)—C$_2$H$_5$, —CH$_2$—CH(CH$_3$)—CH$_2$—CH$_2$—CH$_3$, —CH(CH$_3$)—(CH$_2$)$_3$—CH$_3$, —C(CH$_3$)$_2$—CH$_2$—CH$_2$—CH$_3$, —CH$_2$—C(CH$_3$)$_2$—C$_2$H$_5$, —CH$_2$—CH$_2$—C(CH$_3$)$_3$, —CH(CH$_3$)—CH(CH$_3$)—C$_2$H$_5$, —CH(CH$_3$)—CH$_2$—CH(CH$_3$)$_2$, —C(CH$_3$)$_2$—C(CH$_3$)$_2$, —CH(CH$_3$)—C(CH$_3$)$_3$, —CH$_2$—CH(C$_2$H$_5$)$_2$ and —CH(C$_2$H$_5$)—(CH$_2$)$_2$—CH$_3$.

The compounds embraced by formula I may be prepared by the following methods:

Method A

By reacting a diamine of the formula

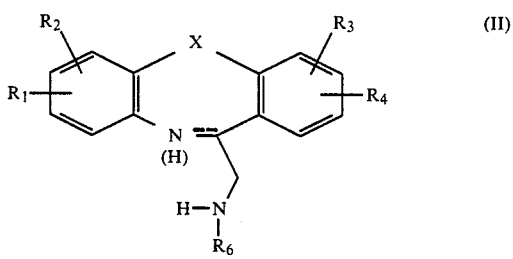

wherein $R_1$, $R_2$, $R_3$, $R_4$, $R_6$, X and the broken line have the meanings previously defined, with a halocyanogen such as bromocyanogen.

This method yields compounds of the formula I wherein $R_5$ is hydrogen.

The reaction is preferably performed at room temperature in a mixture of ethanol and tetrahydrofuran, but may also be carried out in other solvents, for instance in alkanols, chloroform or aromatic hydrocarbons such as toluene, xylene, etc., optionally in the presence of an auxiliary base such as potassium carbonate. The reaction temperatures are widely variable and may be up to the boiling point of the reaction mixture.

When a compound of the formula II is reacted with bromocyanogen, for example, an intermediate of the formula

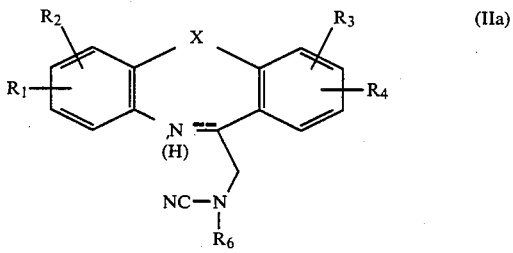

wherein the broken line and the substituents $R_1$ to $R_4$, $R_6$ and X have the meanings previously defined is formed, and this intermediate compound is the actual starting material for the cyclization reaction. However, it is not necessary to isolate this compound since it cyclizes smoothly to yield the desired end product of the formula I.

Some of the diamines of the formula II are known compounds [see J. Med. Chem. 13, 35–39 (1970); or British Pat. No. 1,229,252]; those which are not known may be prepared in analogy to the method there described.

The end products of the formula I wherein $R_5$ is hydrogen obtained by this method may be converted into the corresponding compounds of the formula I wherein $R_5$ is alkyl or alkenyl by alkylation or alkenylation with an alkyl or alkenyl halide or sulfonic acid ester of the formula $$R_5-Y \qquad (III)$$

wherein $R_5$ has the meanings previously defined except hydrogen, and

X is halogen or sulfonyloxy, such as tosyloxy or mesyloxy, in a suitable, preferably polar solvent such as dimethylformamide, and in the presence of a base such as sodium hydride.

Method B

By cyclizing a compound of the formula

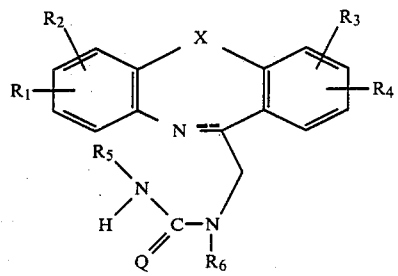

wherein $R_1$, $R_2$, $R_3$, $R_4$, $R_6$, X and the broken line have the meanings previously defined, $R_5$ has the meanings previously defined except hydrogen, and Q is oxygen or sulfur.

The cyclization is effected by the action of an acid halide such as $POCl_3$, optionally in a conventional solvent such as toluene.

An alternative form of this method is S-alkylation of a thiourea derivative of the formula IV (Q=sulfur) to form the corresponding alkylmercapto compound of the formula

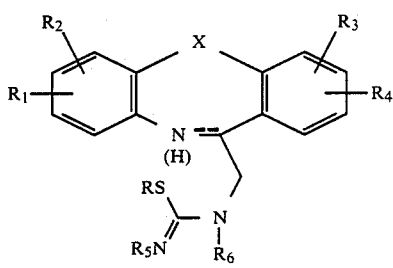

wherein $R_1$ through $R_6$, X and the broken line have the meanings defined in connection with formula IV, and R is optionally substituted alkyl of 1 to 4 carbon atoms, and cyclization thereof by heating it in a conventional solvent, such as ethanol or toluene, or in the molten state, to yield the corresponding compound of the formula I.

The starting compounds of the formula IV are obtained by conventional methods, for instance, by reacting a diamine of formula II with an alkyl isocyanate or an alkyl isothiocyanate with alkyl groups of 1 to 4 carbon atoms.

The reaction products obtained according to these methods are isolated by using known laboratory methods. If desired, the crude products thus obtained may be purified by using special methods, such as column chromatography, before being crystallized in the form of bases or suitable salts.

If desired, racemates obtained according to the invention may be separated into their enantiomers by conventional methods.

Salts obtained initially may optionally be converted into free bases, while free bases obtained initially may optionally be converted into acid addition salts by conventional methods.

The compounds embraced by formula I are basic and, therefore, form addition salts with inorganic or organic acids. Examples of non-toxic, pharmacologically acceptable acid addition salts are those formed with hydrohalic acids, such as hydrochloric acid, hydrobromic acid or hydroiodic acid; sulfuric acid; phosphoric acid; aliphatic or aromatic carboxylic acids, such as acetic acid, tartaric acid, malonic acid, citric acid, fumaric acid or salicylic acid; or sulfonic acids, such as methanesulfonic acid or toluenesulfonic acid.

The following examples illustrate the present invention and will enable others skilled in the art to understand it more completely. It should be understood, however, that the invention is not limited solely to the particular examples given below.

EXAMPLE 1

2-Methyl-3-imino-1,2,9,13b-tetrahydro-3-H-dibenz-[c,f]-imidazo-[1,5-a]-azepine hydrobromide

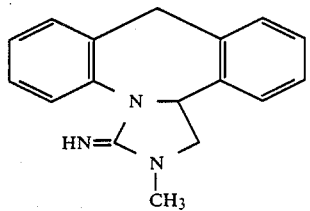

A suspension of 7.15 gm (0.03 mol) of 6-methylaminomethyl-6,11-dihydro-5H-dibenz-[b,e]-azepine [formula II; $R_1$ to $R_4$=H; $R_6$=—$CH_3$; X=—$CH_2$—; broken line=single bond] in 70 ml of absolute ethanol was mixed with a solution of 3.2 gum (0.03 mol) of bromocyanogen in 8 ml of absolute tetrahydrofuran, while stirring. Accompanied by a slightly exothermic reaction, a solution was formed which was stirred after four hours of standing at ambient temperature. The reaction solution was then mixed with ether. The crystals thus obtained were suction-filtered off and dried.

Yield: 8.6 gm (83% of theory)

Melting point: 247°–249° C.

After crystallization from methanol/ethyl acetate, the compound, which was analytically pure, melted at 247° to 250° C.

EXAMPLE 2

2-Methyl-3-imino-2,3-dihydro-9H-dibenz-[c,f]-imidazo-[1,5-a]-azepine hydrobromide

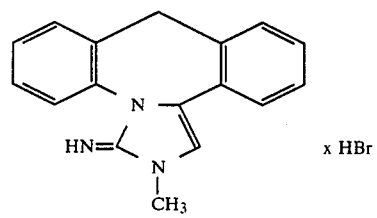

x HBr

A solution of 19.93 gm (0.188 mol) of bromocyanogen in 140 ml of absolute tetrahydrofuran was added dropwise to a solution of 44.4 gm (0.188 mol) of 6-methylaminomethyl-morphanthridine [formula II: dotted line=double bond; $R_1$ to $R_4$=H; $R_6$=—$CH_3$; X=—$CH_2$—], while stirring and cooling with ice. The reaction mixture was stirred at room temperature for four hours more, and was then mixed with ethyl acetate. The crystals obtained thereby were suction-filtered off and dried.

Yield: 49.5 gm (77% of theory);
Melting point: 287°–289° C.

The analytically pure hydrobromide had a melting point of 291° to 293° C. after recrystallization from ethanol/ethyl acetate.

EXAMPLE 3

2-Ethyl-3-imino-1,2,9,13b-tetrahydro-3H-dibenz-[c,f]-imidazo-[1,5-a]-azepine hydrobromide This compound was prepared analogous to Example 1 from the corresponding diamine of the formula II. It had a melting point of 213° to 216° C. (acetonitrile).

EXAMPLE 4

2-Isopropyl-3-imino-1,2,9,13b-tetrahydro-3H-dibenz-[c,f]-imidazo-[1,5-a]-azepine hydrobromide This compound was prepared analogous to Example 1 from the corresponding diamine of the formula II. It had a melting point of 230° to 233° C. (acetonitrile/ether).

EXAMPLE 5

2-Methyl-3-imino-1,2,3-13b-tetrahydrodibenz-[b,f]-imidazo-[1,5-][1,4]-oxazepine hydrochloride

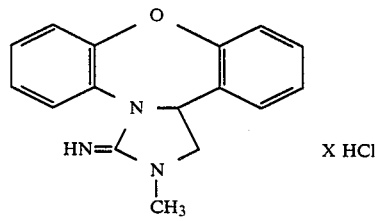

X HCl

This compound was prepared analogous to Example 1 from the corresponding diamine of the formula II. It had a melting point of 297° to 300° C. (ethanol/ethyl acetate).

EXAMPLE 6

2-Methyl-3-imino-1,2,3-13b-tetrahydrodibenz-[b,f]-imidazo-[1,5-d][1,4]-thiazepine hydrobromide

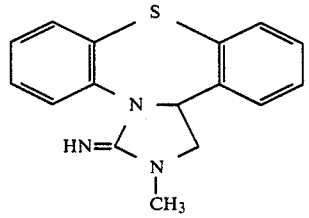

x HBr

This compound was prepared analogous to Example 1 from the corresponding diamine of the formula II. It had a melting point of 204° to 206° C. (ethanol/ethyl acetate).

EXAMPLE 7

2-Ethyl-3-imino-2,3-dihydro-9H-dibenz-[c,f]-imidazo-[1,5-a]-azepine hydrobromide This compound was prepared analogous to Example 2 from the corresponding diamine of the formula II. It had a melting point of 279° to 282° C. (methanol/ether; decomposition).

EXAMPLE 8

2-Allyl-3-imino-2,3-dihydro-9H-dibenz-[c,f]-imidazo-[1,5-a]-azepine hydrobromide This compound was prepared analogous to Example 2 from the corresponding diamine of the formula II. It had a melting point of 244° to 246° C. (methanol/ether).

EXAMPLE 9

2-Isopropyl-3-imino-2,3-dihydro-9H-dibenz-[c,f]-imidazo-[1,5-a]-azepine hydrobromide This compound was prepared analogous to Example 2 from the corresponding diamine of the formula II. It had a melting point of 291° to 294° C. (acetonitrile, decomposition).

EXAMPLE 10

2-Methyl-3-imino-2,3-dihydro-dibenz-[b,f]-imidazo-[1,5-d][1,4]-oxazepine hydrobromide

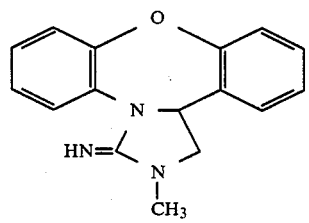

x HBr

This compound was prepared analogous to Example 2 from the corresponding diamine of the formula II. It had a melting point of 296° to 299° C. (methanol/ethyl acetate).

EXAMPLE 11

2-Methyl-3-imino-2,3-dihydro-dibenz-[b,f]-imidazo-[1,5-d][1,4]-thiazepine hydrobromide

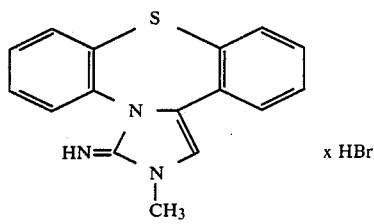

x HBr

This compound was prepared analogous to Example 2 from the corresponding diamine of the formula II. It had a melting point of 314° to 317° C. (methanol/ethyl acetate; decomposition).

The following table shows the additional compounds of the formula

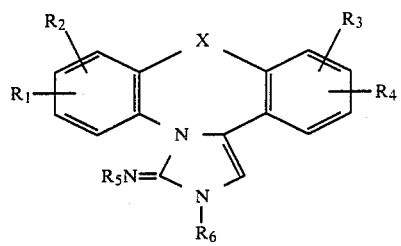

which were prepared in analogy to Example 2:

TABLE I

| Example No. | X | $R_1$ | $R_2$ | $R_3$ | $R_4$ | $R_5$ | $R_6$ |
|---|---|---|---|---|---|---|---|
| 12 | —CH$_2$— | —H | 7-Cl | —H | —H | —H | —CH$_3$ |
| 13 | —CH$_2$— | 6-CH$_3$ | —H | —H | —H | —H | —CH$_3$ |
| 14 | —CH$_2$— | 6-Cl | —H | —H | —H | —H | —C$_2$H$_5$ |
| 15 | —O— | —H | —H | —H | —H | —H | -n-C$_4$H$_9$ |
| 16 | —O— | 6-CH$_3$ | —H | —H | —H | —H | —CH$_3$ |
| 17 | —O— | 6-CH$_3$ | —H | —H | —H | —H | —C$_2$H$_5$ |
| 18 | —O— | 6-CH$_3$ | —H | —H | 12-Cl | —H | —CH$_3$ |
| 19 | —O— | 6-Cl | —H | —H | —H | —H | —CH$_3$ |
| 20 | —O— | 6-Cl | —H | 11-CH$_3$ | —H | —H | —CH$_3$ |
| 21 | —O— | —H | 7-Cl | —H | —H | —H | —CH(CH$_3$)$_2$ |
| 22 | —O— | —H | —H | —H | 12-Cl | —H | —CH$_3$ |
| 23 | —O— | —H | —H | —H | 12-CH$_3$ | —H | —CH$_3$ |
| 24 | —S— | —H | —H | —H | 12-Cl | —H | —CH$_3$ |
| 25 | —S— | —H | —H | —H | 12-CH$_3$ | —H | —CH$_3$ |
| 26 | —S— | —H | 7-CH$_3$ | —H | —H | —H | —CH$_3$ |
| 27 | —S— | 6-CH$_3$ | —H | —H | —H | —H | —CH$_3$ |
| 28 | —S— | 6-CH$_3$ | —H | —H | —H | —H | —C$_2$H$_5$ |
| 29 | —S— | 6-CH$_3$ | —H | —H | 12-CH$_3$ | —H | —CH$_3$ |
| 30 | —S— | 6-Cl | —H | —H | —H | —H | —CH$_3$ |

The following table shows the additional compounds of the formula

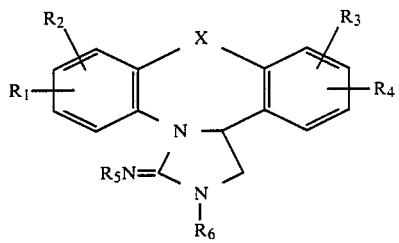

which were prepared in analogy to Example 1:

TABLE II

| Example No. | X | $R_1$ | $R_2$ | $R_3$ | $R_4$ | $R_5$ | $R_6$ |
|---|---|---|---|---|---|---|---|
| 31 | —CH$_2$— | —H | —H | —H | —H | —CH$_3$ | —CH$_3$ |
| 32 | —CH$_2$— | —H | 7-Cl | —H | —H | —H | —CH$_3$ |
| 33 | —CH$_2$— | 6-CH$_3$ | —H | —H | —H | —H | —CH$_3$ |
| 34 | —O— | —H | —H | —H | —H | —C$_2$H$_5$ | —CH$_3$ |
| 35 | —O— | 6-CH$_3$ | —H | —H | —H | —H | —CH$_3$ |
| 36 | —O— | 6-CH$_3$ | —H | —H | —H | —H | —C$_2$H$_5$ |
| 37 | —O— | 6-CH$_3$ | —H | —H | 12-Cl | —H | —CH$_3$ |
| 38 | —O— | 6-Cl | —H | —H | —H | —H | —CH$_3$ |
| 39 | —O— | 6-Cl | —H | 11-CH$_3$ | —H | —H | —CH$_3$ |
| 40 | —O— | —H | 7-Cl | —H | —H | —H | —CH$_3$ |
| 41 | —O— | —H | —H | —H | 12-Cl | —H | —CH$_3$ |
| 42 | —O— | —H | —H | —H | 12-CH$_3$ | —H | —CH$_3$ |
| 43 | —S— | —H | —H | —H | 12-Cl | —H | —CH$_3$ |
| 44 | —S— | —H | —H | —H | 12-CH$_3$ | —H | —CH$_3$ |
| 45 | —S— | —H | 7-CH$_3$ | —H | —H | —H | —CH$_3$ |

TABLE II-continued

| Example No. | X | $R_1$ | $R_2$ | $R_3$ | $R_4$ | $R_5$ | $R_6$ |
|---|---|---|---|---|---|---|---|
| 46 | —S— | 6-CH$_3$ | —H | —H | —H | —H | —CH$_3$ |
| 47 | —S— | 6-CH$_3$ | —H | —H | —H | —CH$_3$ | —C$_2$H$_5$ |
| 48 | —S— | 6-CH$_3$ | —H | —H | 12-CH$_3$ | —H | —CH$_3$ |
| 49 | —S— | 6-Cl | —H | —H | —H | —H | —CH$_3$ |

The compounds of the present invention, that is, those embraced by formula I above, in the form of racemates, pure enantiomers and mixtures of enantiomers, and their non-toxic, pharmacologically acceptable acid addition salts, have useful pharmacodynamic properties. More particularly, they exhibit long-lasting antiallergic, antihistaminic and antiserotininic activities and inhibit blood platelet aggregation in warm-blooded animals such as rats, dogs and monkeys.

By virtue of the above properties the novel compounds are useful for the treatment of reactions caused by the release of histamine or serotonin, bronchial asthma, allergic bronchitis, allergic rhinitis, allergic conjunctivitis and allergic diathases.

The good oral efficacy of the compounds is particularly important for therapeutic purposes. This oral efficacy is also a major advantage over the disodium salt of cromoglycic acid, a much-used commercial product for the treatment of bronchial asthma and allergic bronchitis.

The pharmacological properties of the compounds of this invention were evaluated by various standard test methods, inter alia the following:

(a) Tests on allergized rats were carried out after passive sensitization of the animals with IgE antibodies and subsequent antigen provocation. In this way, passive cutaneous anaphylaxis (PCA) was produced (Goose et al [1969]: Immunology 16, 749).

(b) Antihistaminic activity:
When administered orally and intravenously to rats, dogs and monkeys, the compounds inhibited the histamine wheal produced by the intracutaneous injection of histamine. The results were quantified by measuring the wheal after extravasation of Evans Blue dye into the skin.

The following table shows the results of these tests for an important compound of the invention, which is illustrative of the genus:

TABLE III

| Compound of Example | PCA ED$_{50}$ [mg/kg] (Rat, p.o.) | Histamine Wheal (rat) i.v. | p.o. | LD$_{50}$ [mg/kg] (Mouse, p.o.) |
|---|---|---|---|---|
| 2 | 1.1 | 0.07 | 2.7 | 280 |

For pharmaceutical purposes the compounds of the present invention are administered to warm-blooded animals perorally, parenterally, rectally, by inhalation or topically as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories, creams, ointments, lotions, aerosols and the like. An effective amount of the compounds according to the present invention is from 0.002 to 0.57 mgm/kg body weight, preferably 0.007 to 0.14 mgm/kg body weight for oral administration. For inhalation, it is 0.0007 to 0.28 mgm/kg body weight, preferably 0.002 to 0.07 mgm/kg body weight, by means of conventional inhalation compositions, especially metered aerosols and capsules for powder inhalation.

The indicated dosages may be administered several times daily.

The following examples illustrate a few pharmaceutical compositions comprising a compound of the present invention as an active ingredient and represent the best modes contemplated of using the invention. The parts are parts by weight unless otherwise specified.

EXAMPLE 50

Tablets 200 mgm-tablets are prepared in conventional manner from the following ingredients:

| | |
|---|---|
| 2-Methyl-3-imino-2,3-dihydro-9H—dibenz-[c,f]-imidazo-[1,5-a]-azepine hydrobromide | 0.005 parts |
| Stearic acid | 0.001 " |
| Dextose | 0.194 " |
| | 0.200 parts |

EXAMPLE 51

Aerosol for inhalation

The aerosol is prepared in conventional manner from the following ingredients:

| | |
|---|---|
| 2-Methyl-3-imino-2,3-dihydro-9H—dibenz-[c,f]-imidazo-[1,5-a]-azepine hydrobromide | 1.00 parts |
| Soybean lecithin | 0.20 " |
| Propellent gas mixture (Frigen 11, 12 and 114) | q.s.ad 100.00 " |

The composition is filled into aerosol containers with a metering valve, the individual stroke of which is designed to release a dose of 0.5 mg of the active ingredient.

EXAMPLE 52

Capsules for inhalation

The end product of Example 2 is micronized (particle size mainly between 2 and 6 μm), optionally with the addition of micronized carriers such as lactose, and then filled into hard gelatin capsules. The composition is inhaled by means of conventional apparatus for powder inhalation. Each capsule contains, for example, between 0.2 and 20 mg of active substance and from 0 to 40 mg of lactose.

EXAMPLE 53

Ointment

The ointment is prepared in conventional manner from the following ingredients:

| | | |
|---|---|---|
| 2-Methyl-3-imino-2,3-dihydro-9H—dibenz-[c,f]-imidazo-[1,5-a]-azepine hydrobromide | 2.000 | parts |
| Fuming hydrochloric acid | 0.011 | " |
| Sodium pyrosulfite | 0.050 | " |
| Mixture of equal parts of cetyl alcohol and stearyl alcohol | 20.000 | " |
| White vaseline | 5.000 | " |
| Synthetic bergamot oil | 0.075 | " |
| Distilled water | q.s. ad 100.000 | " |

Any one of the other compounds embraced by formula I or a non-toxic, pharmacologically acceptable acid addition salt thereof may be substituted for the particular active ingredient in Examples 50 through 53. Likewise, the amount of active ingredient in these illustrative examples may be varied to achieve the dosage range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

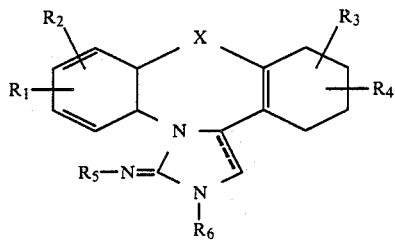

wherein $R_1$, $R_2$, $R_3$ and $R_4$ are each hydrogen, halogen, alkyl of 1 to 6 carbon atoms or alkoxy of 1 to 6 carbon atoms;

$R_5$ is hydrogen, alkyl of 1 to 6 carbon atoms or alkenyl of 3 to 6 carbon atoms;

$R_6$ is alkyl of 1 to 6 carbon atoms, alkenyl of 3 to 6 carbon atoms, phenyl, halo-phenyl, lower alkyl-phenyl, or lower alkoxy-phenyl or

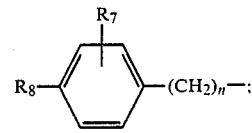

$R_7$ and $R_8$ are each hydrogen, halogen, alkyl of 1 to 6 carbon atoms or alkoxy of 1 to 6 carbon atoms;

n is an integer from 0 to 4, inclusive;

X is —O—, —S— or —$CH_2$—; and the broken line between the 1- and 13b-positions indicates a single or double bond;

or a non-toxic, pharmacologically acceptable acid addition salt thereof.

2. A compound of claim 1, where

X and the broken line have the meanings defined in claim 1, $R_1$, $R_2$, $R_3$, $R_4$ and $R_5$ are hydrogen, and $R_6$ is alkyl of 1 to 3 carbon atoms, or a non-toxic, pharmacologically acceptable acid addition salt thereof.

3. A compound of claim 1, which is 2-methyl-3-imino-2,3-dihydro-9H-dibenz-[c,f]-imidazo-[1,5-a]-azepine or a non-toxic, pharmacologically acceptable acid addition salt thereof.

4. An antiallergic or antithrombotic pharmaceutical composition consisting essentially of an inert pharmaceutical carrier and an effective antiallergic or antithrombotic amount of a compound of claim 1.

5. The method of suppressing allergic reactions or relieving thrombosis in a warm-blooded animal, which comprises perorally, parenterally, rectally or topically administering to said animal an effective antiallergic or antithrombotic amount of a compound of claim 1.

* * * * *